United States Patent [19]

Wu

[11] Patent Number: 4,618,359
[45] Date of Patent: Oct. 21, 1986

[54] HETEROCYCLIC ESTERS OF PHENOXYBENZOIC ACIDS USEFUL AS HERBICIDES

[75] Inventor: Frank Wu, Libertyville, Ill.

[73] Assignee: Sandoz Ltd., Basel, Switzerland

[21] Appl. No.: 715,442

[22] Filed: Mar. 25, 1985

Related U.S. Application Data

[63] Continuation-in-part of Ser. No. 475,414, Mar. 14, 1983, abandoned, which is a continuation-in-part of Ser. No. 351,697, Feb. 24, 1982, abandoned.

[51] Int. Cl.$^4$ .................... A01N 43/08; C07D 307/04
[52] U.S. Cl. ........................................ 71/88; 549/420; 549/475
[58] Field of Search ............................ 549/475; 71/88

[56] References Cited

U.S. PATENT DOCUMENTS 4,063,929 12/1977 Bayer et al. ..................... 71/115

FOREIGN PATENT DOCUMENTS 0021692 7/1981 European Pat. Off. .

Primary Examiner—Nicky Chan
Attorney, Agent, or Firm—Gerald D. Sharkin; Richard E. Vila

[57] ABSTRACT

New herbicidal chemical compounds of the formula:

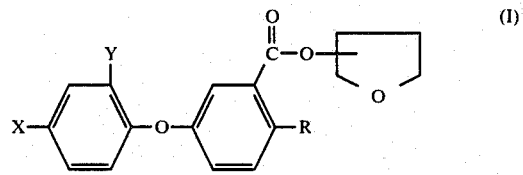

wherein X is trifluoromethyl; Y is selected from the group consisting of hydrogen, halogen, nitro and cyano and R is selected from the group consisting of nitro, alkylthio, halogen and cyano; herbicidal compositions thereof and methods of controlling weeds therewith. The compound, 3-tetrahydrofuryl 2-nitro-5-(2-chloro-4-trifluoromethylphenoxy) benzoate, is particularly useful for the control of the weed, velvetleaf, and safe to corn and soybean. Velvetleaf is found in corn and soybean crops and its presence will lower the yield of these crops.

9 Claims, No Drawings

HETEROCYCLIC ESTERS OF PHENOXYBENZOIC ACIDS USEFUL AS HERBICIDES

This application is a continuation-in-part of my copending application, Ser. No. 475,414, filed Mar. 14, 1983 now abandoned; which is a continuation-in-part of my application Ser. No. 351,697, filed Feb. 24, 1982, now abandoned.

This invention relates to new compositions of matter and more specifically relates to new chemical compounds of the formula:

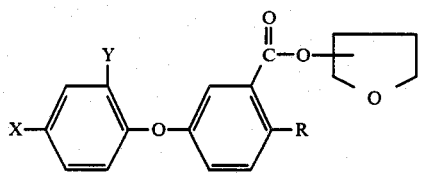
(I)

wherein X is trifluoromethyl; Y is selected from the group consisting of hydrogen, halogen, nitro and cyano and R is selected from the group consisting of nitro, alkylthio, halogen and cyano.

The compounds of the present invention are unexpectedly useful as selective herbicides.

In a preferred embodiment of the present invention, Y is halogen.

The compounds of the present invention can be prepared by reacting acid chloride of the formula:

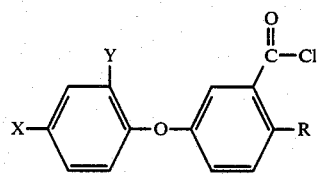
(II)

wherein X, Y and R are as heretofore described, with an alcohol of the formula:

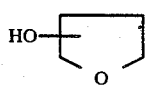
(III)

wherein n is the integer 1 or 2, in the presence of an acid acceptor such as a tertiary amine. This reaction can be effected by combining about equimolar amounts of the acid chloride and alcohol in an inert organic reaction medium such as toluene. Preferably, excess molar amounts of acid acceptor is used to ensure removal of the hydrogen chloride that is formed. Typically, the reaction is carried out at room temperature with agitation. After completion of the reaction, the desired product can be recovered by first removing acid acceptor salt followed by evaporation of the solvent used as the reaction medium. This product can then be used as such or can be further purified by conventional techniques.

The acid chloride of formula II, useful in preparing the compounds of this invention, can be readily prepared from the corresponding acids by reaction with thionyl chloride.

Exemplary precursor acid for the acid chlorides of formula II are 2-nitro-5-(2-chloro-4-trifluoromethylphenoxy)benzoic acid, 2-nitro-5-(2-bromo-4-trifluoromethylphenoxy)benzoic acid, 2-nitro-5-(2,4-dichlorophenoxy)benzoic acid, 2-nitro-5-(2-cyano-4-trifluoromethylphenoxy)benzoic acid, 2-nitro-5-(4-trifluoromethylphenoxy)benzoic acid, 2-methylthio-5-(2-chloro-4-trifluoromethylphenoxy)benzoic acid, 2-chloro-5-(2-chloro-4-trifluoromethylphenoxy)benzoic acid, 2-bromo-5-(2-chloro-4-trifluoromethylphenoxy)benzoic acid, 2-ethylthio-5-(2-chloro-4-trifluoromethylphenoxy)benzoic acid, 2-propylthio-5-(2-chloro-4-trifluoromethylphenoxy)benzoic acid, 2-cyano-5-(2-chloro-4-trifluoromethylphenoxy)benzoic acid in like.

The compounds of the present invention, wherein the tetrahydrofuran or tetrahydropyran moieties are attached to the carboxylic acid group in the 2-position, are preferably prepared by reacting the acid corresponding to formula II with dihydrofuran or 3,4-dihydropyran. This reaction can be effected by combining the acid and the dihydrofuran at room temperature in the presence of a catalytic amount of p-toluenesulfonic acid. The use of excess pyran or furan is preferred. After the reaction is completed, the mixture can be washed and stripped of excess starting material to yield the desired product.

The manner in which the compounds of this invention can be prepared is more specifically illustrated in the following examples.

EXAMPLE 1

Preparation of 2-Nitro-5-(2-chloro-4-trifluoromethylphenoxy)benzoyl chloride

2-Nitro-5-(2-chloro-4-trifluoromethylphenoxy)benzoic acid (80 grams) and toluene (80 ml) were charged into a reaction vessel equipped with a mechanical stirrer, thermometer and reflux condenser. Thionyl chloride (80 ml) was slowly added at room temperature with stirring. After the addition was completed, the mixture was heated at reflux with continued stirring for a period of one hour. Stirring was thereafter continued at room temperature overnight. After this time the reaction mixture was stripped of toluene to yield the desired product as an oil.

EXAMPLE 2

Preparation of 3-Tetrahydrofuryl 2-Nitro-5-(2-chloro-4-trifluoromethylphenoxy)benzoate 3-Hydroxytetrahydrofuran (1.76 grams; 0.02 mole), toluene (50 ml) and triethylamine (2.0 grams; 0.02 mole) were charged into a glass reaction vessel equipped with a mechanical stirrer and addition funnel. A solution of 2-nitro-5-(2-chloro-4-trifluoromethylphenoxy)benzoyl chloride (7.60 grams; 0.02 mole) in toluene (10 ml) was slowly added with stirring. After the addition was completed, stirring was continued overnight. After this time, the reaction mixture was washed with water and dried over anhydrous sodium sulfate. The dried solution was then stripped of solvent under reduced pressure leaving a brown oil. This oil was purified by silica gel chromatography using toluene and ethyl acetate/toluene mixtures as the eluant. The purified oil was triturated in ethanol to yield the desired product 3-tetrahydrofuryl 2-nitro-5-(2-chloro-4-trifluoromethylphenoxy)benzoate as a white solid, melting point at 55° C.

EXAMPLE 3

Preparation of 3-Tetrahydrofuryl 2-Nitro-5-(2-bromo-4-trifluoromethylphenoxy)benzoate 3-Hydrotetrahydrofuran (0.04 mole), toluene (50 ml) and triethylamine (0.04 mole) are charged into a glass reaction vessel equipped with a mechanical stirrer and addition funnel. A solution of 2-nitro-5-(2-bromo-4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-nitro-5-(2-bromo-4-trifluoromethylphenoxy)benzoate.

EXAMPLE 4

Preparation of 3-Tetrahydrofuryl 2-Nitro-5-(2-nitro-4-trifluoromethylphenoxy)benzoate 3-Hydroxytetrahydrofuran (0.04 mole), toluene (50 ml) and triethylamine (0.04 mole) are charged into a glass reaction vessel equipped with a mechanical stirrer and adtition funnel. A solution of 2-nitro-5-(2-nitro-4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-nitro-5-(2-nitro-4-trifluoromethylphenoxy)benzoate.

EXAMPLE 5

Preparation of 3-Tetrahydrofuryl 2-Nitro-5-(2-cyano-4-trifluoromethylphenoxy)benzoate 3-Hydroxytetrahydrofuran (0.04 mole), toluene (50 ml) and triethylamine (0.04 mole) are charged into a glass reaction vessel equipped with a mechanical stirrer and addition funnel. A solution of 2-nitro-5-(2-cyano-4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-nitro-5-(2-cyano-4-trifluoromethylphenoxy)benzoate.

EXAMPLE 6

Preparation of 3-Tetrahydrofuryl 2-Methylthio-5-(4-trifluoromethylphenoxy)benzoate 3-Hydroxytetrahydrofuran (0.04 mole), toluene (50 ml) and triethylamine (0.04 mole) are charged into a glass reaction vessel equipped with a mechanical stirrer and addition funnel. A solution of 2-methylthio-5-(4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-methylthio-5-(4-trifluoromethylphenoxy)benzoate.

EXAMPLE 7

Preparation of 3-Tetrahydrofuryl 2-chloro-5-(2-bromo-4-trifluoromethylphenoxy)benzoate 3-Hydroxytetrahydrofuran (0.04 mole), toluene (50 ml) and triethylamine (0.04 mole) are charged into a glass reaction vessel equipped with a mechanical stirrer and addition funnel. A solution of 2-chloro-5-(2-bromo-4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-chloro-5-(2-bromo-4-trifluoromethylphenoxy)benzoate.

EXAMPLE 8

Preparation of 3-Tetrahydrofuryl 2-Bromo-5-(2-Chloro-4-trifluoromethylphenoxy)benzoate 3-Hydroxytetrahydrofuran (0.04 mole), toluene (50 ml) and triethylamine (0.04 mole) are charged into a glass reaction vessel equipped with a mechanical stirrer and addition funnel. A solution of 2-bromo-5-(2-chloro-4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-bromo-5-(2-chloro-4-trifluoromethylphenoxy)benzoate.

EXAMPLE 9

Preparation of 3-Tetrahydrofuryl 2-Cyano-5-(2,4-dichlorophenoxy)benzoate

3-Hydroxytetrahydrofuran (0.04 mole), toluene (50 ml) and triethylamine (0.04 mole) are charged into a glass reaction vessel equipped with a mechanical stirrer and addition funnel. A solution of 2-cyano-5-(2,4-dichlorophenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-cyano-5-(2,4l -dichlorophenoxy)benzoate.

EXAMPLE 10

Preparation of 3-Tetrahydrofuryl 2-Ethylthio-5-(2-Chloro-4-bromophenoxy)benzoate 3-Hydroxytetrahydrofuran (0.04 mole), toluene (50 ml) and triethylamine (0.04 mole) are charged into a glass reaction vessel equipped with a mechanical stirrer and addition funnel. A solution of 2-ethylthio-5-(2-chloro-4-bromophenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent under reduced pressure leaving a residue. This residue is purified by silica gel chromatography using toluene and ethyl acetate/toluene mixture as the eluant to yield the desired product 3-tetrahydrofuryl 2-ethylthio-5-(2-chloro-4-bromophenoxy)benzoate.

EXAMPLE 11

Preparation of 3-Tetrahydropyranyl 2-(Methylthio-5-(2-Chloro-4-trifluoromethylphenoxy)-benzoate 3-Hydroxytetrahydropyran (0.04 mole), toluene (50 ml) and triethylamine (0.04 mole) are charged into a glass reaction vessel equipped with a mechanical stirrer and addition funnel. A solution of 2-nitro-5-(2-chloro-4-trifluoromethylphenoxy)benzoyl chloride (0.04 mole) in toluene (20 ml) is slowly added at room temperature with stirring. After the addition is completed, stirring is continued for a period of about eight hours. After this time, the reaction mixture is washed with water and dried over anhydrous magnesium sulfate. The dried solution is then stripped of solvent is then stripped of solvent under reduced pressure leaving a residue. This residue is purified by silica gel chromatography using toluene and ethyl acetate/toluene mixture as the eluant to yield the desired product 3-tetrahydropyranyl 2-methylthio-5-(2-chloro-4-trifluoromethylphenoxy)benzoate.

EXAMPLE 12

Preparation of 2-Tetrahydrofuryl 2-Nitro-5-(2-Chloro-4-trifluoromethylphenoxy)benzoate Dihydrofuran (0.03 mole), 2-nitro-5-(2-chloro-4-trifluoromethylphenoxy)benzoic acid (0.025 mole), methylene chloride (25 ml) and p-toluenesulfonic acid (1 spatula tip) are charged into a glass reaction vessel equipped with a magnetic stirrer. The reaction mixture is stirred at room temperature until the carboxylic acid group can no longer be detected by IR in the mixture. After this time, the reaction mixture is washed with dilute aqueous sodium carbonate and with water. The washed solution was dried and stripped of solvent and unreacted starting material to yield the desired product 2-tetrahydrofuryl 2-nitro-5-(2-chloro-4-trifluoromethylphenoxy)benzoate.

For practical use as herbicides, the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under superatmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems, an inverted emulsion (water in oil) can be prepared for direct application to weed infestations.

A typical herbicidal composition, according to this invention, is illustrated by the following example in which the quantities are in parts by weight.

EXAMPLE 13

| Preparation of a Dust | |
|---|---|
| Product of Example 2 | 10 |
| Powdered Talc | 90 |

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compounds of the present invention are also useful when combined with other herbicides and/or defoliants, dessicants, growth inhibitors and the like in the herbicidal compositions heretobefore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and the plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPP, 2,4,5-TB, 2,4,5-TES, 3,4-DA, silvex and the like; carbamate, herbicides such as IPC, CIPC, swep, barban, BCPC, CEPC, CPPC, and the like; thiocarbamate and dithiocarbamate herbicides such as DCEC, methan sodium, EPTX, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,N-dimethylacetamide, CDEA, CDAA, alpha-chloro-N-isopropylacetamide, 2-chloro-N-isopropylacetanilide, 4-(chloroacetyl)-morpholine, 1-(chloracetyl)piperidine, and the like; chlorinated aliphatic acid herbicides such as TCA, dalapon, 2,3-dichloropropionic acid, 2,2,3-TPA and the like; chlorinated benzoic acid and the phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlorobenil, DPA, diphenamid, dipropalin, trifluraline, solan, dicryl, merphos, DMPA, DSMA, MSMA, potassium azide, acrolein, benefin, bensulide, AMS, bromacil, 2-(3,4-dichlorophenyl)-4-methyl-1,2,4-oxadiazolidine, 3,5-dione, bromoxynil, cacodylic acid, DMA, DPMF, cypromid, DCB, DCPA, dichlone, diphenatril, DMTT, DNAP, EBEP, EXD, HCA, ioxynil, IPX, isocyil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindone B, propanil and the like.

Such herbicides can also be used in the methods and composition of this invention in the form of their salts, esters, amides, and other derivatives whenever applicable to the particular parent compounds.

Weeds are undesirable plants growing where they are not wanted, having no economic value, and interfering with the production of cultivated crop, with the growing of ornamental plants, or with the welfare of livestock. Many types of weeds are known, including annuals such as pigweed, lambsquarter, foxtail, crabgrass, wild mustard, field pennycress, ryegrass, goose grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after the seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0=no injury, 1, 2=slight injury, 3, 4=moderate injury, 5, 6=moderately severe injury, 7, 8, 9=severe injury, 10=death and NE indicated not emerged. The effectiveness of these compounds is demonstrated by the following date set out in Tables I and II. Numbers with decimal places are the result of averaging two or more ratings obtained from replicate experiments.

The herbicidal activity of the compounds of this invention was also demonstrated by experiments carried out for the post-emergence control of a variety of weeds. In these experiments the compounds to be tested were formulated as aqueous emulsions and sprayed at the indicated dosge on the foliage of the various weed species that have attained a prescribed size. After spraying, the plants were placed in a greenhouse and watered daily or more frequently. Water was not applied to the foliage of the treated plants. The severity of the injury was determined 10 to 15 days after treatment and was rated on the scale of from 0 to 10 heretobefore described. The effectiveness of these compounds is demonstrated by the following data set forth in Tables III and IV. Values with decimal places again are the result of averaging of replicate experiments.

TABLE I

Pre-Emergence Screen
14 & 21-Day Tests

| Compound | #/Acre | WMSD 14 | 21 | BDWD 14 | 21 | PIGW 14 | 12 | JMWD 14 | 21 | VTLF 14 | 21 | MNGY 14 | 21 | YLFX 14 | 21 | BNGS 14 | 21 | JNGS 14 | 21 | QKGS 14 | 21 | WOAT 14 | 21 |
|---|---|---|---|---|---|---|---|---|---|---|---|---|---|---|---|---|---|---|---|---|---|---|---|
| Product of Ex. 2 | 1 | 10 | 10 | 9 | 9 | 10 | 10 | NE | NE | 10 | 10 | 10 | 10 | 10 | 10 | 10 | 10 | 10 | 10 | 10 | 10 | 3 | 5 |
|  | .5 | 10 | 10 | 7 | 8 | 10 | 10 | NE | NE | 10 | 10 | 10 | 10 | 10 | 10 | 9 | 10 | 10 | 10 | 10 | 5 | 4 | 1 |
|  | .25 | 10 | 10 | 8 | 10 | 10 | 10 | NE | NE | NE | NE | 9 | 9 | 10 | 10 | 10 | 10 | 5 | 10 | 0 | 0 | 0 | 0 |
|  | .125 | 10 | 10 | 0 | 0 | 9 | 9 | NE | NE | 0 | 0 | 6 | 0 | 7 | 2 | 8 | 3 | 0 | 2 | 0 | 0 | 0 | 0 |

| Compound | #/Acre | CBGS 14 | 21 | SPGT 14 | 21 | CTGS 14 | 21 | SUBT 14 | 21 | SOYB 14 | 21 | COTN 14 | 21 | PTBN 14 | 21 | ALFA 14 | 21 | WHT 14 | 21 | RICE 14 | 21 | SORG 14 | 21 | CORN 14 | 21 | OAT 14 | 21 |
|---|---|---|---|---|---|---|---|---|---|---|---|---|---|---|---|---|---|---|---|---|---|---|---|---|---|---|---|
| Product of Ex. 2 | 1 | NE | NE | 10 | 10 | 5 | 5 | 10 | 10 | 9 | 7 | 9 | 9 | 10 | 10 | 10 | 10 | 6 | 2 | 10 | 10 | 10 | 10 | 5 | 1 | 1 | 3 |
|  | .5 | 9 | NE | 9 | 10 | 0 | 0 | 10 | 10 | 7 | 4 | 6 | 5 | 10 | 10 | 10 | 10 | 3 | 0 | 10 | 10 | 10 | 10 | 5 | 2 | 1 | 1 |
|  | .25 | 10 | 10 | 9 | 10 | 0 | 0 | 10 | 10 | 3 | 2 | 0 | 0 | 0 | 0 | 8 | 5 | 0 | 0 | 10 | 10 | 6 | 7 | 3 | 0 | 0 | 0 |
|  | .125 | 8 | 7 | 5 | 0 | 0 | 0 | 9 | 10 | 0 | 0 | 0 | 0 | 0 | 0 | 3 | 0 | 0 | 0 | 4 | 0 | 1 | 1 | 0 | 0 | 0 | 0 |

TABLE II

Post-Emergence Screen

| Compound Product of Example 2 | | INJURY RATING | | |
|---|---|---|---|---|
| WEED SPECIES | #/ACRE 1 | .5 | .25 | .125 |
| WMSD | 10 | 10 | 10 | 10 |
| BDWD | 10 | 10 | 10 | 10 |
| PIGW | 10 | 10 | 10 | 10 |
| JMWD | 10 | 10 | 10 | 10 |
| VTLF | 10 | 10 | 10 | 10 |
| MNGY | 10 | 10 | 10 | 10 |
| YLFX | 10 | 10 | 10 | 3 |
| BNGS | 10 | 10 | 10 | 10 |
| JNGS | 10 | 10 | 10 | 10 |
| QKGS | 10 | 10 | 9 | 3 |
| WOAT | 10 | 10 | 5 | 2 |
| CBGS | 10 | 10 | 10 | 10 |
| SPGT | 10 | 10 | 10 | 10 |
| CTGS | 8 | 2 | 1 | 0 |
| SUBT | 10 | 10 | 10 | 10 |
| COTN | 10 | 10 | 10 | 10 |
| SOYB | 10 | 7 | 6 | 4 |
| PTBN | 10 | 5 | 7 | 6 |
| ALFA | 10 | 10 | 10 | 10 |
| SORG | 10 | 10 | 9 | 4 |
| WHT | 10 | 10 | 1 | 1 |
| RICE | 5 | 1 | 0 | 0 |
| CORN | 1 | 5 | 9 | 0 |
| OAT | 10 | 10 | 2 | 0 |

Abbreviations For Weeds
WMSD = Wild Mustard
BDWD = Bindweed
PIGW = Pigweed
JMWD = Jimsonweed
VTLF = Velvetleaf
MNGY = Morningglory
YLFX = Yellow Foxtail
BNGS = Barnyardgrass
JNGS = Johnsongrass
QKGS = Quickgrass
WOAT = Wild Oat
CBGS = Crabgrass
SPGT = Sprangletop
CTGS = Cheatgrass
SUBT = Sugarbeet
COTN = Cotton
SOYB = Soybean
PTBN = Pintobean
ALFA = Alfalfa
SORG = Sorgum
WHT = Wheat The following herbicidal test data demonstrates the particular value of the compound, 3-tetrahydrofuryl 2-nitro-5-(2-chloro-4-trifluoromethylphenoxy)benzoate (Product of Example 2) for the control of the weed velvetleaf, a weed that is prevalent in corn, soybeans and other cash crops. The presence of velvetleaf in these crops will significantly lower the yield of the crops.

For this use this compound is most effectively applied as a post-emergence herbicide by contacting the weeds or the locus of said weeds. As the following herbicidal test data demonstrates, it is effective for the control of weeds at rates of application of from about 0.25 to about 1.0 pounds per acre. It is particularly effective at rates of about 0.25 to 0.50 pounds per acre.

In each test the instant compound was compared with test results obtained by using commercial products. As can be seen from the results reported in TABLE III, the product gave more improved velvetleaf control than obtained from the commercial products.

TABLE III

Post-Emergence Herbicidal Control of Velvetleaf in Soybeans*

| COMPOUND | TIME OF APPLICATION | VELVETLEAF CONTROL | SOYBEAN PHYTO-TOXICITY** | SOYBEAN YIELD Lbs./Acre | TEST RATE Lbs./Acre |
|---|---|---|---|---|---|
| Product of Example 2 | One Trifoliant Leaf is Fully Expanded | 8.5 | 0.0 | 28.1 | 0.25 |
| Product of Example 2 | One Trifoliant Leaf is Fully Expanded | 9.0 | 0.2 | 29.3 | 0.50 |
| Product of Example 2 | One Trifoliant Leaf is Fully Expanded | 9.7 | 0.4 | 29.4 | 1.0 |
| Product of Example 2 | Three Trifoliant Leaves are Fully Expanded | 8.2 | 0.0 | 29.4 | 0.25 |
| Product of Example 2 | Three Trifoliant Leaves are Fully Expanded | 9.1 | 0.2 | 26.9 | 0.50 |
| Product of Example 2 | Three Trifoliant Leaves are Fully Expanded | 9.7 | 0.6 | 28.6 | 1.00 |
| Sodium Salt of Acifluorfen | One Trifoliant Leaf is Fully Expanded | 6.3 | 0.0 | 29.6 | 0.5 |
| Sodium Salt of Acifluorfen | Three Trifoliant Leaves are Fully Expanded | 7.5 | 0.0 | 31.0 | 0.5 |
| ALACHLOR | Three Trifoliant Leaves are Fully Expanded | 1.1 | 0.0 | 22.6 | 2.5 |
| Untreated | Three Trifoliant Leaves are Fully Expanded | 0.0 | 0.0 | 11.9 | — |

*ALL DATA AVERAGE OF FOUR REPLICATES
**SOYBEAN PHYTOTOXICITY DATA AVERAGE OF FOUR REPLICATES AT 30 DAYS AND 90 DAYS AFTER TREATMENT

TABLE IV

Post-Emergence Herbicidal Control of Velvetleaf in Corn*

| COMPOUND | TEST RATE Lbs./Acre | TIME OF APPLICATION | VELVETLEAF CONTROL | CORN PHYTOTOXICITY** | CORN YIELD Lbs./Acre |
|---|---|---|---|---|---|
| Product of Example 2 | 0.25 | Bewteen Spike and 5 in. Height | 9.0 | 0.0 | 112.5 |
| Product of Example 2 | 0.50 | Between Spike and 5 in. Height | 8.8 | 0.8 | 115.7 |
| Product of Example 2 | 1.0 | Between Spike and 5 in. Height | 9.6 | 1.4 | 115.2 |
| Product of Example 2 | 0.25 | Between 5 & 10 in. Height | 9.6 | 0.7 | 99.1 |
| Product of Example 2 | 0.50 | Between 5 & 10 in. Height | 8.9 | 0.5 | 116.1 |
| Product of Example 2 | 1.0 | Between 5 & 10 in. Height | 9.5 | 1.9 | 107.9 |
| Dimethylamine Salt of Dicamba | 0.25 | Between Spike and 5 in. Height | 9.0 | 0.0 | 120.0 |
| Dimethylamine Salt of Dicamba | 0.25 | Between 5 & 10 in. Height | 8.0 | 0.6 | 118.0 |
| ALACHLOR | 2.5 | Between Spike and 5 in. Height | 1.9 | 0 | 100.2 |
| Untreated | 0 |  | 0 | 0 | 50.1 |

*ALL DATA AVERAGE OF FOUR REPLICATES
**CORN PHYTOTOXICITY DATA AVERAGE OF FOUR REPLICATES AT 30, 60 & 90 DAYS AFTER TREATMENT

I claim:

1. 3-Tetrahydrofuryl 2-nitro-5-(2-chloro-4-trifluoromethylphenoxy)benzoate.

2. A herbicidal composition comprising an inert carrier and a herbicidally toxic amount of the compound of claim 1.

3. A method of controlling weeds which comprises contacting said weeds or the locus of said weeds with a toxic amount of herbicidal composition of claim 2.

4. The method of claim 3 wherein the weeds are dicot plants.

5. The method of claim 3 wherein the weed is velvetleaf.

6. The method of claim 5 wherein the velvetleaf is in the presence of soybean plants.

7. The method of claim 5 wherein the velvetleaf is in the presence of corn plants.

8. The method of claim 3 wherein the toxic amount is from about one-fourth to about one pound per acre.

9. The method of claim 3 wherein the toxic amount is from about one-fourth to about one-half pounds per acre.

* * * * *